(12) United States Patent
Jespersen et al.

(10) Patent No.: US 9,075,243 B2
(45) Date of Patent: Jul. 7, 2015

(54) METHOD AND SYSTEM FOR ULTRASHORT PULSE FIBER DELIVERY USING HIGHER ORDER MODE FIBER

(75) Inventors: Kim G. Jespersen, Lyngby (DK); Tuan Le, Vienna (AT)

(73) Assignee: OFS FITEL, LLC, Norcross, GA (US)

(*) Notice: Subject to any disclaimer, the term of this patent is extended or adjusted under 35 U.S.C. 154(b) by 489 days.

(21) Appl. No.: 13/372,419

(22) Filed: Feb. 13, 2012

(65) Prior Publication Data

US 2012/0224597 A1 Sep. 6, 2012

Related U.S. Application Data

(60) Provisional application No. 61/447,895, filed on Mar. 1, 2011.

(51) Int. Cl.

| | |
|---|---|
| G02B 6/26 | (2006.01) |
| G02B 6/42 | (2006.01) |
| G02B 23/24 | (2006.01) |
| G01N 21/3581 | (2014.01) |
| H01S 3/00 | (2006.01) |
| G02F 1/35 | (2006.01) |
| G02B 6/28 | (2006.01) |
| G02B 6/12 | (2006.01) |
| G02B 6/293 | (2006.01) |
| A61B 5/00 | (2006.01) |
| G01N 21/3586 | (2014.01) |

(52) U.S. Cl.
CPC .......... *G02B 23/2469* (2013.01); *G02B 6/2861* (2013.01); *G02B 6/12007* (2013.01); *G02B 6/29395* (2013.01); *G01N 21/3581* (2013.01); *A61B 5/0082* (2013.01); *H01S 3/0057* (2013.01); *H01S 3/0092* (2013.01); *G02F 1/3513* (2013.01); *G01N 21/3586* (2013.01)

(58) Field of Classification Search
None
See application file for complete search history.

(56) References Cited

U.S. PATENT DOCUMENTS

| | | | |
|---|---|---|---|
| 7,529,278 B2 * | 5/2009 | Liu | 372/6 |
| 2008/0138011 A1 * | 6/2008 | Ramachandran | 385/27 |

* cited by examiner

*Primary Examiner* — Ryan Lepisto
*Assistant Examiner* — Erin Chiem
(74) *Attorney, Agent, or Firm* — Mandelbaum Salsburg

(57) ABSTRACT

Embodiments of the present invention describe systems and methods for delivering ultrashort laser pulses through an optical fiber system with higher order mode fiber output and without pre-chirping. In one embodiment of the present invention, an all-fiber delivery system comprises a mode-locked solid-state or fiber laser for generating laser pulses in the 0.2 μm to 1.3 μm wavelength range, a single mode fiber with normal dispersion, and a long-period-grating mode converter, and a higher order mode fiber with anomalous dispersion, wherein the all-fiber delivery system is free of bulk optics, and propagates laser pulses without pulse pre-chirping, and wherein higher order mode output beam from the all-fiber delivery system comprises pulses at less than about 200 femtoseconds.

13 Claims, 7 Drawing Sheets

METHOD AND SYSTEM FOR ULTRASHORT PULSE FIBER DELIVERY USING HIGHER ORDER MODE FIBER

CROSS-REFERENCE TO RELATED APPLICATIONS

The present application claims priority to U.S. Provisional Patent Application No. 61/447,895, entitled "Method and System for Large Distance Ultrashort Pulse Fiber Delivery without Pre-Chirping," filed Mar. 1, 2011, the disclosure of which is incorporated by reference herein.

BACKGROUND

1. Field of the Invention

Embodiments of the present invention describe systems and methods for applications using sub 200 fs laser pulses in the NIR, e.g. for non-linear microscopy or generating Terahertz (THz) radiation, using a fiber delivery with a higher order mode ($LP_{02}$) fiber output without pre-chirping.

Pre-chirping in the context of this document shall refer to a method that intentionally introduces anomalous dispersion with bulk optics prior to the fiber delivery with the aim to obtain shortest possible pulse durations right after the fiber delivery output. Further bulk optical components like gratings, prisms, grisms and dispersive mirrors and so on, are referred to as any arrangements de-coupled from the fiber delivery module that are supposed to partly or fully compensate the dispersion of the involved optical fibers.

2. Description of the Related Art

Delivery of ultrashort laser pulses in the near infrared wavelength range is attracting more and more attention due to the rising number of industrial and medical applications that utilize very short optical pulses to outperform conventional measurement methods in speed, quality and resolution, and due to the fact that femtosecond light sources have been matured in their size, stability and user friendliness. However, in all cases the high flexibility of a fiber link is required, and such a fiber link is difficult to make using standard fibers commercially available and without using pre-chirping with bulk optical components. One example is generation of THz pulses. Generation of THz pulses is very efficient in the NIR wavelength range using fs laser pulses. There are commercial and practical interests in having a fiber delivery that enables transport of femtosecond pulses from the light source to a THz system. THz generation in industrial applications is typically for security purposes (detection of explosives or dangerous liquids) or for material inspection.

Fiber delivery of ultrashort pulses in the 800 nm and 1030 nm wavelength range is traditionally done using a normal dispersive fiber such as a standard-single mode fiber or LMA fiber in combination with a bulk optic dispersive element. The dispersive element has anomalous dispersion that matches the normal dispersion of the fiber and ideally provides net zero group delay dispersion. The bulk optic dispersive element introduces a chirp to the pulse prior to launching into the fiber, which compensates the chirp that will be introduced in the normal dispersive fiber; hence, the term "pre-chirping." The bulk optic anomalous dispersive element typically comprises diffraction gratings, prisms, combination of gratings and prisms, or chirped mirrors, and contribute significantly to the cost, size, and practical use in terms of alignment and stability of the fiber delivery system.

Many different technological approaches have been reported that facilitate the transmission of laser pulses in the NIR by optical fibers. In one example, 82 fs light pulses at 800 nm were demonstrated after altogether 0.75 m of single mode fiber by use of a combination of temporal and spectral compression. In another example, by the help of a grating compressor, 140 fs pulses can travel through a 1.3 m microstructured fiber. In another example, without pre-chirping, 170 fs pulses were delivered through a hollow-core photonic crystal fiber (PCF). Using the large dispersion of a higher order mode fiber, sub 150 fs laser pulses were sent over 2 m of optical fiber in another example. In yet another example, 25 fs light pulses were obtained after 1.6 m optical fiber by using dispersive mirrors and gratings for pre-chirping. The same approach facilitates 160 fs laser pulses to pass through 45 m optical fiber with transmission efficiencies up to 40%. However, fiber delivery of laser pulses shorter than 200 fs generally has to rely on pre-chirping with space consuming and alignment sensitive bulk optics.

In addition, MultiPhoton Fluorescence Microscopy is a technique to obtain a very precise image, e.g., of biological samples, using a light source of twice the wavelength or higher multiple of the wavelength. The idea is to utilize a narrow focus and short optical pulses such that 2 or more photons will excite the sample at a very well defined location, e.g., at the very center of the focused light. Only light in this well-defined volume will have enough intensity to excite the sample with two or more photons simultaneously and generate fluorescence. If you would use light at the fundamental wavelength using only one photon to excite the sample, you would get fluorescence from all over the place and your image gets blurred.

Thus, there is a need for systems and methods to deliver sub 200 fs laser pulses in the NIR through an optical fiber without the need for pre-chirping with bulk optics.

SUMMARY

Embodiments of the present invention describe systems and methods for delivering femtosecond laser pulses using optical fibers with higher order mode fiber output without pre-chirping.

In one embodiment of the present invention, an all-fiber delivery system comprises a single mode fiber with normal dispersion, and a higher order mode fiber with anomalous dispersion; wherein the all-fiber delivery system is free of bulk optics, and propagates laser pulses, without pulse pre-chirping.

In another embodiment of the present invention, an all-fiber delivery system comprises a mode-locked Ti:Sapphire laser or frequency doubled erbium doped fiber laser for generating laser pulses, a single mode fiber with normal dispersion, and a long-period-grating (LPG) mode converter, and a higher order mode fiber with anomalous dispersion, having an effective area of about 14.9 µm2, wherein the all-fiber delivery system is free of bulk optics, and propagates laser pulses in the 800 nm wavelength range over 1 to 50 meters, without pulse pre-chirping, and wherein an output pulse from the all-fiber delivery system comprises pulses at less than about 200 femtoseconds, having an energy between about 1 pJ to about 10 nJ.

In yet another embodiment of the present invention, a method for generating and detecting terahertz radiation comprises: providing an all-fiber delivery system comprising a Ti:Sapphire mode-locked laser or frequency doubled mode-locked Erbium doped fiber laser for generating laser pulses, a single mode fiber with normal dispersion, and a higher order mode fiber with anomalous dispersion, wherein the all-fiber delivery system is free of bulk optics; generating an input laser pulse from the laser centered at about 800 nm; propagating the input laser pulses from a fundamental mode to a higher order mode; and outputting output pulses at less than about 200 femtoseconds; wherein the method operates free of any pre-chirping of the input laser pulse.

BRIEF DESCRIPTION OF THE DRAWINGS

So the manner in which the above-recited features of the present invention can be understood in detail, a more particular description of embodiments of the present invention, briefly summarized above, may be had by reference to embodiments, which are illustrated in the appended drawings. It is to be noted, however, the appended drawings illustrate only typical embodiments of embodiments encompassed within the scope of the present invention, and, therefore, are not to be considered limiting, for the present invention may admit to other equally effective embodiments, wherein.

Figure 1:
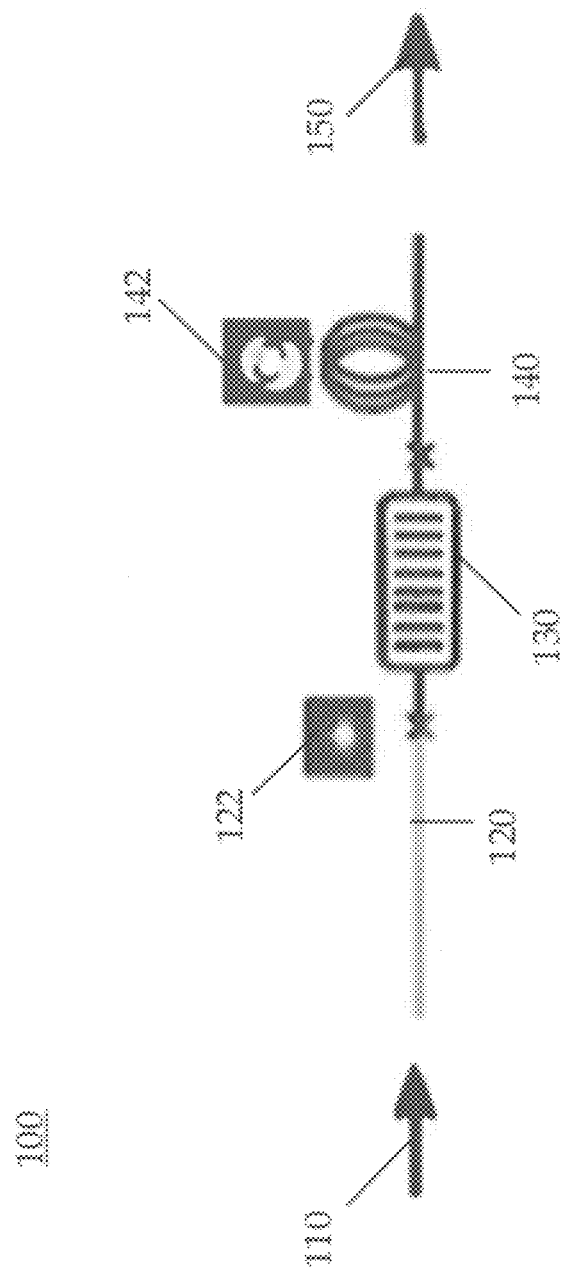
FIG. 1 depicts an ultrashort pulse fiber delivery system in accordance with one embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

Embodiments of the present invention describe systems and methods for femtosecond laser applications using fiber delivery with higher order mode fiber output without pre-chirping.

As used herein, the term "about" or "approximately," or derivatives thereof, when referencing a numerical value, should be deemed to include within ten percent of such numerical value in either direction. In addition, when such terms are utilized to described absolutes (e.g., zero), the absolute should be deemed to include within one unit of reasonable measurement in either direction, as would ordinarily be used by those of ordinary skill in the art.

Fiber delivery of ultrashort laser pulses that are subject to normal fiber dispersion is traditionally restricted to distances below a few meters which is due to the application of dispersion compensating devices that are not capable of managing third and higher order material dispersion. However, by the use of a fiber delivery concept based on higher order mode fibers, those ultrashort laser pulses are transmitted over arbitrary several tens of meters without the need for pulse pre-chirping in accordance with embodiments of the present invention.

In one embodiment, ultrashort laser pulses in the 800 nm wavelength range are transmitted over 20 meters without the need for pulse pre-chirping in accordance with embodiments of the present invention. As such, embodiments of the present invention may be utilized to reveal the potential for remote THz imaging or spectroscopy using ultrashort laser pulses, and application of the fiber delivery may be demonstrated by generating and detecting broadband THz radiation at the fiber output.

Generally, in its basic form, embodiments of the present invention comprise a fiber delivery system having a first fiber with normal dispersion followed by a higher order mode (HOM) fiber with anomalous dispersion. In certain embodiments, the first fiber with normal dispersion may comprise a single mode fiber, a micro-structure fiber, or other multi-mode fiber, capable of providing a similar function, i.e., having normal dispersion. In one embodiment, a special multi-mode fiber may be the HOM fiber itself where light is propagating in the fundamental mode. In this instance, the HOM fiber can be configured to couple light into the fundamental mode and propagate for some distance with normal dispersion before reaching a grating. At this point, the HOM fiber is then configured to propagate the light in the $LP_{02}$ mode, or other higher order mode, with anomalous dispersion.

The group delay dispersion, i.e. the accumulated $\beta_2$ (more specifically $\Sigma(\beta_2 \cdot L)$, where the sum is over the different fiber sections and L is the length of each section) and the ratio $\beta_3/\beta_2$ of the two fiber sections are matched to have zero net group delay dispersion and minimum accumulated higher order dispersion (i.e., third order dispersion (TOD)), respectively. In many embodiments, the fiber delivery system provides pulse delivery directly from an oscillator to a fs-laser application, where the output of the fiber is in the $LP_{02}$ mode.

Other embodiments of the present invention provide for THz generation and optically gated detection of the THz pulse electric field using a variety of techniques. For example, in one embodiment, THz generation may include using a poled slap of dielectric (e.g. GaAs) or utilizing optical rectification in an appropriate crystal such as (ZnTe or GaP). In other embodiments, detection can be done using an optically gated electrical circuit (i.e., semiconductor material with electrodes) or using electrooptic response, e.g., using ZnTe, where the polarization of a detection pulse is altered due to the THz pulse, which is also known as electrooptic sampling.

Embodiments of the present invention may generally utilize a higher order mode fiber. A higher order mode (HOM) fiber generally exploits propagation in a specific higher order mode, allowing for a large variety of new fiber properties that are not practical or prohibited in fiber designs with propagation in the fundamental mode only. Hence, LMA-HOM fibers with higher order mode effective areas up to 3200 µm², as well as fibers with high dispersion may be utilized to alienate nonlinearities.

Furthermore, HOM fibers with anomalous dispersion below the zero dispersion wavelength of silica may be utilized and implemented with embodiments of the present invention in connection with ultrashort pulsed laser oscillators for dispersion management. In the 800 nm or 1030 nm wavelength range, embodiments of the present invention may utilize the anomalous dispersion of an HOM fiber to deliver ultrashort laser pulses directly from the laser without the need for pre-chirping with additional anomalous dispersive bulk optics.

FIG. 1 depicts an, ultrashort pulse fiber delivery system in accordance with one embodiment of the present invention. The system 100 generally comprises an input 110 (e.g. a pulse generator, such as a laser), a first fiber 120, a second fiber 140, an output 150, and optionally, a mode converter 130 between the first fiber 120 and the second fiber 140.

The input 110 may comprise any type of pulse signal generator, such as a laser, suitable for embodiments of the present invention. In some embodiments, the input 110 comprises a mode-locked laser. In one exemplary embodiment, the input 110 comprises a Ti:Sapphire mode-locked laser with a repetition rate of 264 MHz, a spectral bandwidth of 6 nm full-width at half maximum (FWHM), and an average output power of 210 mW. In such an exemplary embodiment, the laser light may be centered at about 770 nm.

Optionally, pulses from the input 110 are sent through an optical isolator (e.g., EOT BB8-5X) to prevents back reflection into the pulse source. However, in many instances, the isolator may be omitted if the fiber ends of the system 100 are angle polished. In order to alienate nonlinear effects in the first section of the fiber, a glass block, such as a 5 cm SF 57 glass block is used to stretch the pulses before the light is focused into the fiber by a f=7.5 mm lens. It should be noted, such a glass block is not considered a pre-chirping element, like traditional bulk optic components, such as diffraction gratings, prisms, or chirped mirrors that introduce negative group delay dispersion. In many embodiments, in front of the lens, the pulse duration is estimated to be 350 fs, which may also account for the optical isolator.

In many embodiments, the first fiber 120 comprises a single-mode fiber (SMF). In some embodiments, the first fiber 120 comprises a silica-core fiber having a cladding and/or coating thereon. In one exemplary embodiment, the first fiber 120 comprises a silica-core fiber having a silica cladding and acrylate coating thereon, and is commercially sold by OFS Fitel, of Norcross, Ga., under a "ClearLite 780-11" trademark. In alternative embodiments, as introduced above, the first fiber may also comprise a micro-structured fiber, other multi-mode fiber, the $LP_{01}$ mode of the HOM fiber as described above, or the like.

The second fiber 140 generally comprises a HOM fiber. In one embodiment, the effective area of the HOM fiber is calculated from pre-form data to be 14.9 $\mu m^2$ at 770 nm. For comparison, the effective area in index guiding micro-structured fibers with anomalous dispersion in the near infrared is generally of the order of 2-5 $\mu m^2$. The relatively large effective area means that the non-linear length can be increased by 3-8 times (assuming similar dispersion values) by using the described HOM fiber with embodiments of the present invention.

The mode converter 130 may generally be any type of mode converter suitable for embodiments of the present invention, often depending on the nature of the modes utilized by the system. In one embodiment, the mode converter 130 comprises a long-period-grating (LPG) mode converter positioned in between the first fiber 120 and the second fiber 140. The mode converter comprises a spectral bandwidth sufficiently broad in order to support the full spectral contents of femtosecond pulses. In one embodiment, such broad band mode conversion can be obtained by inscribing the long period grating in a fiber where the group velocities of the two modes to be coupled at a wavelength $\lambda_{TAP}$, are the same. As used herein, $\lambda_{TAP}$ is the wavelength where the phase matching curve attains its extremum point.

The output 150 may comprise any structure or device that may be suitable to receive an output pulse generated from the systems and methods disclosed herein. In many embodiments, the output 150 may comprise free space, wherein the light output may enter the free space, for example, in the far field in a higher order mode. In some embodiments, the output 150 may comprise a second mode converter, similar to the mode converters described above. In addition to those mode converters described above, in one embodiment, the second mode converter may comprise a phase plate written into the output end-face of the higher order mode fiber or mounted directly onto the output end-face of the higher order mode fiber. Whereas the applications of embodiments of the present invention are quite vast, the output 150 should not be limited to any specific structure or component.

As shown in the Figure, the first fiber 120 may comprise a first mode 122 in which the fiber 120 propagates a signal therethrough. In accordance with many embodiments of the present invention. In one embodiment, the first mode 122 comprises a fundamental mode ($LP_{01}$). In alternative embodiments, the first mode 122 may comprise a higher order mode, e.g., $LP_{02}$, $LP_{03}$ or $LP_{04}$, provided, however, normal dispersion can be attained.

The second fiber 140 may similarly comprise a second mode 142. In many embodiments, the second mode 142 may comprise a high order mode with anomalous dispersion, e.g., $LP_{02}$, $LP_{03}$, $LP_{04}$, at which the second fiber 140 may propagate a signal therethrough. In some embodiments, the mode converter 130 may convert the modes, for example, from $LP_{01}$ to $LP_{02}$, for proper operation of the system 100.

Figure 2:
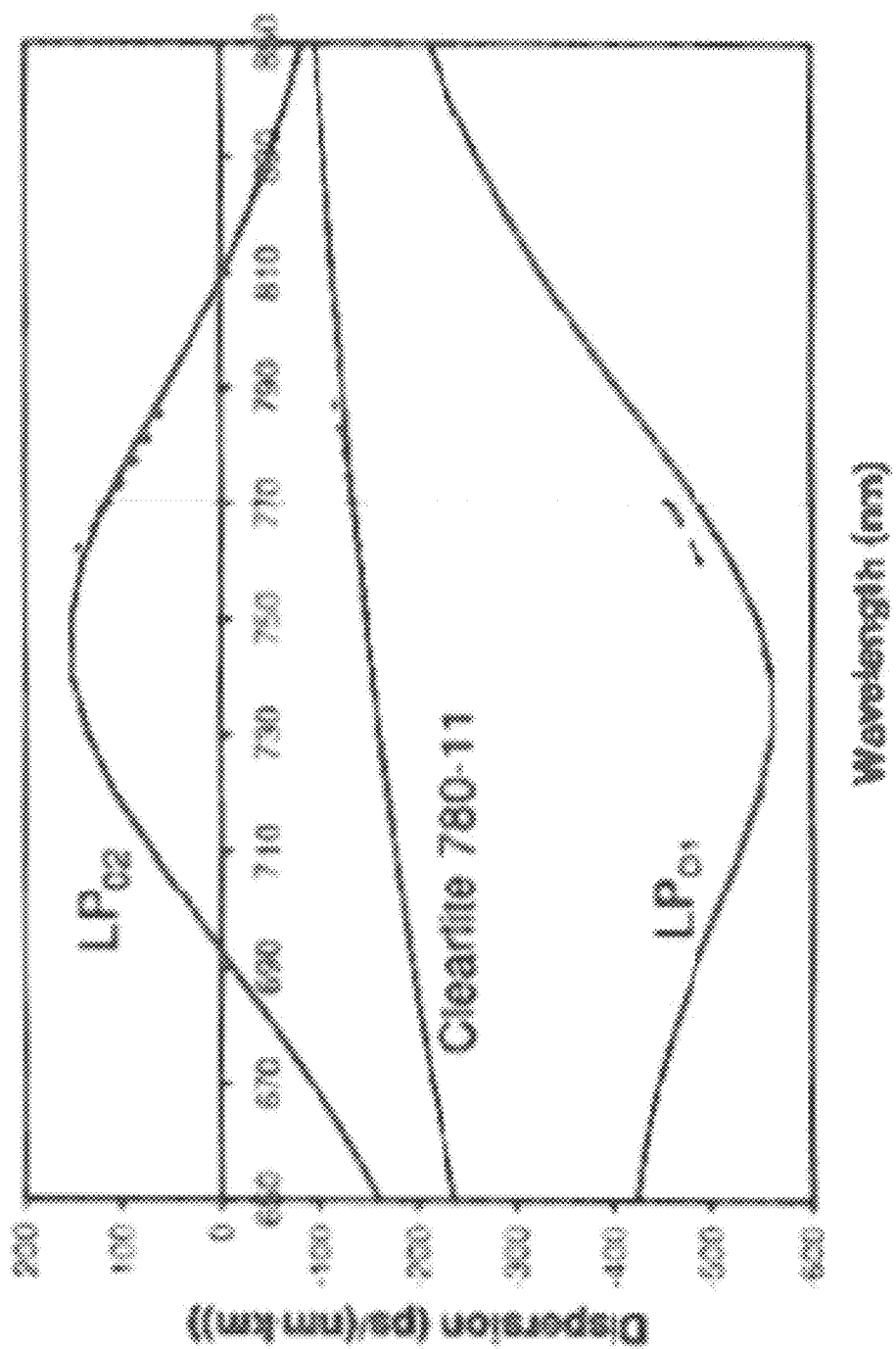
FIG. 2 depicts dispersion curves as calculated from a refractive index profile of a fiber pre-form of LP02 HOM, LP01 fundamental mode, and a single mode fiber (ClearLite 780-11, OFS product), in accordance with one embodiment of the present invention.

FIG. 2 depicts dispersion curves as calculated from a refractive index profile of a fiber pre-form of $LP_{02}$ HOM, $LP_{01}$ fundamental mode, and a single mode fiber, in accordance with one exemplary embodiment of the present invention. In the exemplary embodiment shown, the dispersion of the $LP_{01}$ and $LP_{02}$ modes are calculated from the index profile of a relevant pre-form portion using a scalar mode solver. As shown, the HOM $LP_{02}$ dispersion at about 770 nm is found to be about D=+112.7 ps/(nm km) with a dispersion slope of about S=−2.542 ps(nm$^2$ km). This corresponds to a second and third order dispersion (TOD) of about $\beta_2$=−0.0355 ps$^2$/m and about $\beta_3$=−0.0002229 ps$^3$/m, respectively.

Additionally, as shown in the Figure, the fundamental $LP_{01}$ mode has a high normal dispersion of about D=−456.9 ps$^2$/(nm km) (corresponding to about $\beta_2$=+0.144 ps$^2$/m) due to the combination of high material dispersion and high normal waveguide dispersion. For comparison, the dispersion of the SMF at about 770 nm is measured to be about D=−135.71 ps$^2$/(nm km) (corresponding to about $\beta_2$=+0.0427 ps$^2$/m). The SMF dispersion slope and TOD are about S=+0.591 ps/(nm$^2$ km) and about $\beta_3$=+0.0000236 ps$^3$/m, respectively. In the exemplary embodiment, the SMF comprises a match-clad fiber type with a dispersion dominated by the material dispersion of silica.

In this embodiment, the second order dispersion of the $LP_{02}$ and the SMF are approximately of the same magnitude with opposite sign $\beta_2$=−0.0355 ps$^2$/m for the $LP_{02}$ and $\beta_2$=+0.0427 ps$^2$/m for the SMF). Furthermore, the ratios $\beta_3/\beta_2$ for the $LP_{02}$ and SMF sections are of approximately same magnitude and equal sign such that when combining fiber sections of $LP_{02}$ and SMF, the higher order dispersion is partly compensated ($\beta_3/\beta_2$=+0.00628 ps for the $LP_{02}$ and $\beta_3/\beta_2$=+0.000553 ps for the SMF).

It should also be noted, in the exemplary embodiment, the length of the HOM fiber relative to the single mode pigtail fibers can be varied to obtain a net dispersion, also known as group delay dispersion, that meets the requirements of a specific application. In the fiber delivery demonstration utilized in the exemplary embodiment, the length of the single mode fiber was trimmed such that the complete delivery length was about 19 m with a net group delay dispersion near zero.

In the exemplary embodiment, light from a femtosecond-laser is coupled into the single-mode end of the fiber module. After travelling through about 9 m of single-mode fiber the signal is coupled into the HOM fiber by the mode converter and exits the fiber module in a $LP_{02}$ mode. In one embodiment, re-collimation is performed by a 25× microscope objective. In the example, in order to define the polarization state for the pulse duration measurement, a manual fiber polarization controller is placed at the single-mode fiber section. Autocorrelation measurements show that the pulse duration becomes abruptly shorter if the pulse energy is above 190 pJ, i.e., pulse peak power in the order of 1.2 kW and 50 mW mean power out of the fiber module. This intensity dependent effect is known as soliton compression.

Pulse propagation can be divided into either (1) linear propagation, where the pulse duration is stretched and compressed according to the dispersion of the fibers; or (2) soliton propagation (also known as nonlinear propagation), where intensity dependent effects together with dispersive effects will alter the pulse duration and spectrum. The nonlinear regime is reached above a certain threshold peak power. In one embodiment the fiber delivery will be subject to linear pulse propagation, and the group delay dispersion and higher order dispersion of the single-mode fiber is chosen to match that of the HOM fiber in order to obtain ideally a Fourier limited output pulse. At long fiber delivery lengths, corresponding to another embodiment, pulse duration in the linear regime may be limited by build-up of uncompensated higher order dispersion. In this case it may be an advantage to increase the peak power and exploit soliton compression to reduce the pulse duration. Soliton formation occurs in fibers with anomalous dispersion, and the effect is often accompanied by Raman scattering in the case of ultrashort pulses. Both, linear pulse propagation and soliton propagation is utilized in the embodiments of the present invention.

Figure 3:
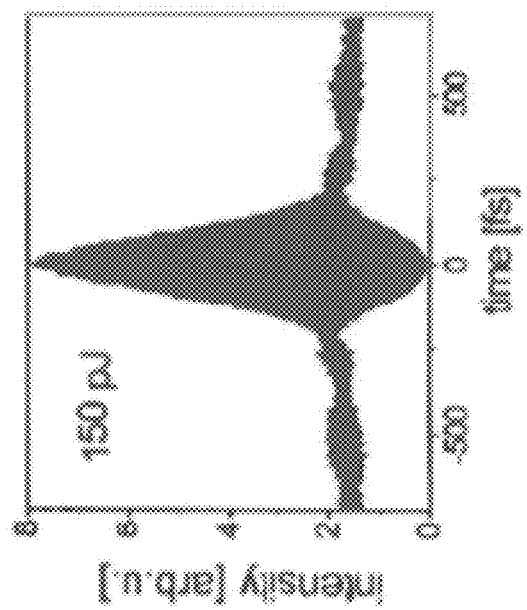
FIG. 3 depicts a fringe resolved autocorrelation of optical pulses delivered by the fiber module, shown by nonlinear pulse compression and by linear dispersion compensation, in accordance with one embodiment of the present invention.
Figure 3:
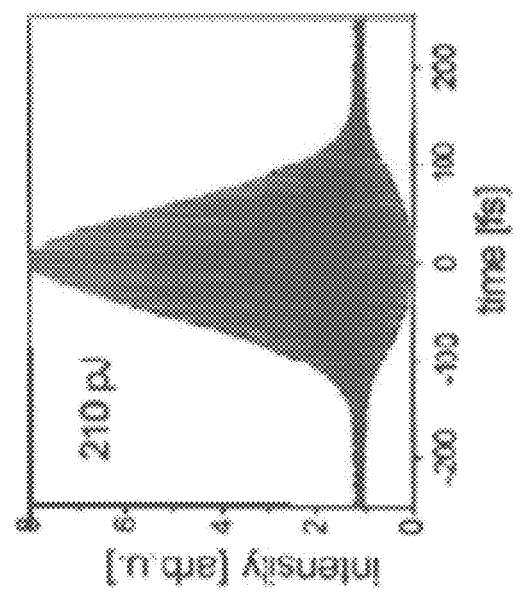

FIG. 3 depicts a fringe resolved autocorrelation of optical pulses delivered by the fiber module in accordance with one embodiment of the present invention. As is shown in FIG. 3 (left), for fiber delivered 210 pJ pulses, a 77 fs pulse is measured within a 0.5 ps time frame with no evidence of a chirp, i.e., remaining uncompensated second and third order dispersion (TOD). In contrast, the same case at 150 pJ pulse energy as shown in FIG. 3 (right) indicates a pronounced chirp, as the ratio of the trace deviates significantly from 8:1 with typical characteristics of excessive TOD.

In accordance with embodiments of the present invention, a single-mode fiber may be attached to the output end of the HOM fiber in order to achieve fundamental mode or $LP_{01}$ mode beam output by the fiber delivery. In many embodiments, group velocity dispersion (GVD) compensated or fourier transform limited optical pulses occur within a section of the HOM fiber that potentially triggers unwanted additional nonlinearities. Therefore, the delivered power is limited by a threshold for nonlinear effects with respect to the peak power. In contrast, in the fiber delivery as depicted in FIG. 1, the optical pulses are further chirped as they travel along the single-mode fiber and start to get shorter when they enter the HOM fiber section. In embodiments of the present invention, there are generally no sections within the fiber delivery where the pulses are dispersion compensated other than towards the end of the fiber delivery. Thus, pulses with higher pulse energies can be delivered. Furthermore the LPG, having a smallest mode-field diameter, for example around 3.6 µm, compared to the HOM and single-mode fiber is located at a position where the chirp is largest, thus avoiding additional conditions for nonlinearities In another embodiment a second SMF section is added at the end of the fiber link comprising a second mode converter for converting the higher order mode to the fundamental mode. In this embodiment the net group delay dispersion is constrained to about zero resulting in a dispersion map along the complete fiber link such that the pulse will be close to Fourier transform limited and attain its highest peak power at a certain location within the higher order mode fiber section. Thus, conditions for nonlinearities are avoided by transmitting pulses with energies lower than the nonlinearity threshold.

In the exemplary embodiment described hereinabove, a Raman induced soliton pulse propagation in the HOM fiber may be observed above a threshold pulse energy if the group delay dispersion of the SMF fiber plus LPG mode converter is smaller than the group delay dispersion of the HOM fiber, i.e. a short pulse is formed inside the HOM fiber before the pulse reaches the end of the HOM fiber. In accordance with the exemplary embodiment, when exceeding an average power of 50 mW a shifting soliton is generated, coexisting with the residual pump pulse, an effect also known as soliton self-frequency shift.

Whereas the HOM fiber generally has anomalous dispersion, the chirp generated by the nonlinear frequency shift is compensated by the fiber dispersion. Thus, the optical pulse behaves similar to a soliton that travels without pulse broadening through the anomalous fiber. The peak power required for fundamental soliton propagation can often be found by comparing the dispersion length and the nonlinear length, an effect widely used at wavelengths above 1.3 µm with standard single mode fibers.

In micro-structured fibers, i.e., so-called "holey fibers," soliton pulse formation can generally be shown for 1.06 µm and 800 nm. In the case of the exemplary embodiment, when the threshold pulse energy (190 pJ) is not reached no chirp-free optical pulses are observed. However, as soon as the pulse energy becomes high enough, the formation of soliton pulse propagation leads to 77 fs optical pulses leaving the HOM fiber.

In accordance with embodiments of the present invention, numerical simulations indicate that Raman scattering may be a main contributor to soliton forming as has been identified herein. A simplified explanation is that in anomalous fibers shorter wavelengths travel faster than components with longer wavelengths. In the presence of Raman scattering, however, the shorter wavelengths are slowed down due to being converted to longer wavelengths which results in temporal pulse compression and a more red shifted spectrum. As a result, only those spectral components that take part in Raman scattering will generally travel or shift with the soliton.

In theory, all other parts are not in "coherence" and therefore travel faster, separating themselves from the soliton. As observed by distant sidelobes in the measured autocorrelation of FIG. 4 (left). Usually, the stronger the nonlinearity or the Raman shift, the larger becomes the separation in time. In contrast, pulse formation and intensity of the sidelobes depend largely, if not solely, on linear pulse compression. Therefore, in case of a shorter single-mode fiber soliton formation happens earlier in the HOM fiber. Hence the sidelobes become more and more chirped due to an unbalanced dispersion matching, and are less evident when the soliton reaches the end of the HOM fiber.

Figure 4:
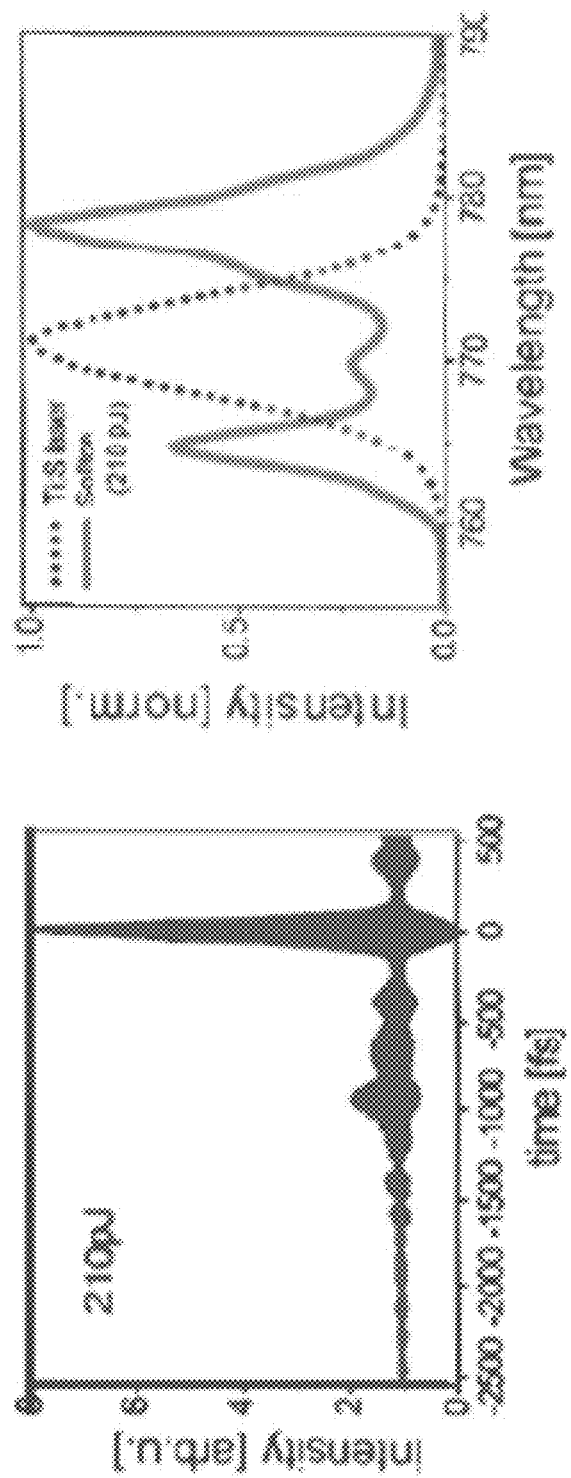
FIG. 4 depicts a graph extending the time window of FIG. 3 to 3 ps, and a spectra of the pulses before and after the fiber module, in accordance with one embodiment of the present invention.

In the exemplary embodiment, however, the pronounced sidelobes in FIG. 4 (left) likely originate from a sufficiently good second order dispersion matching between the HOM and the single-mode fiber.

Figure 5:
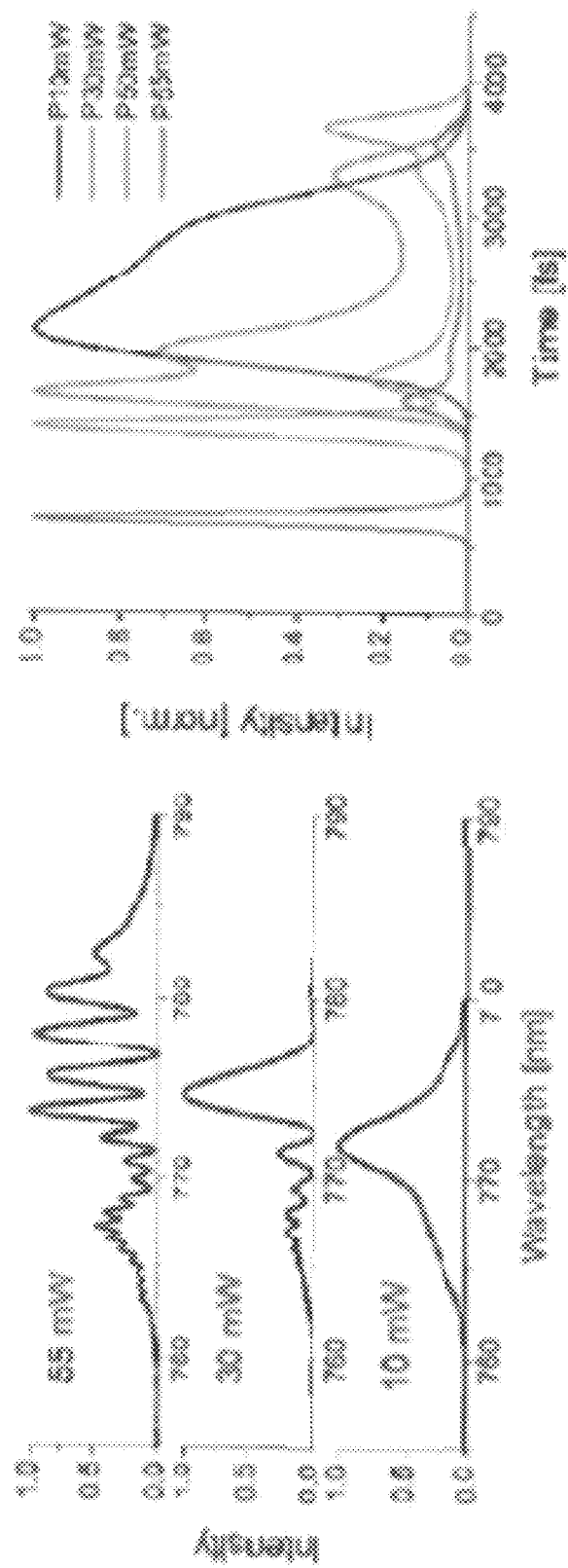
FIG. 5 depicts a spectral and temporal shape of pulses travelling through the fiber module at pulse energies between 40 pJ and 210 pJ in accordance with embodiments of the present invention.

FIG. 5 depicts a spectral and temporal shape of pulses, calculated by a generalized non-linear Schrödinger equation using the split-step method, as they are travelling through the fiber module at pulse energies between 40 pJ and 210 pJ in accordance with exemplary embodiments of the present invention. The pulse energies 40 pJ and 210 pJ correspond to output powers from 10 mW to 55 mW from a mode-locked Ti:Sapphire laser operating at 260 MHz.

In order to qualitatively reproduce results obtained in the experimental embodiments described herein, the length of the single-mode fiber is chosen such that the net group delay dispersion is slightly negative and the soliton is formed toward the end of the HOM fiber, i.e. the group delay dispersion of the single-mode fiber is not much smaller than the HOM fiber. Such effect would justify the relatively low temporal broadening of the pulses at 10 mW shown in FIG. 5 (right) that reflects the case of linear dispersion compression. As power increases, energy is depleted from the linearly chirped pulse and transferred to the soliton by Raman shifting as illustrated by the change of spectral intensity shown in FIG. 5 (left) and reflected by the measured spectrum shown in FIG. 4 (right). In addition, the experimental results also show that without accounting for Raman shifting in the modeling, no soliton may be formed in the fiber.

Figure 6:
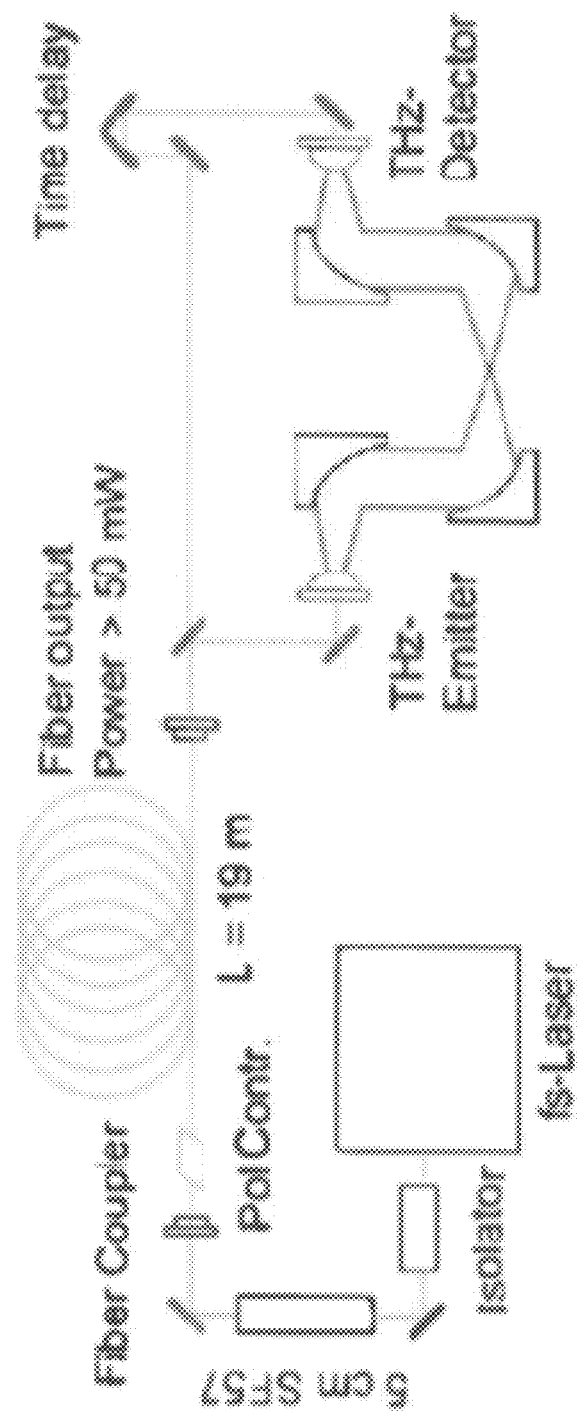
FIG. 6 depicts a schematic showing how fs-laser pulses from a Ti:Sapphire laser are fiber delivered to a THz time-domain spectrometer in accordance with embodiments of the present invention.

FIG. 6 depicts a schematic showing how fs-laser pulses from a Ti:Sapphire laser are fiber delivered to a THz time-domain spectrometer in accordance with embodiments of the present invention. As schematically shown in FIG. 6, the fiber delivery module is attached to a standard THz-TDS system, designed for the use of a femtosecond Ti:Sapphire laser. In one embodiment, the output of the laser is split into a THz generation and a THz detection arm, but this could as well be a system with two separate fiber deliveries for the THz generation and THz detection, respectively. However, in accordance with embodiments of the present invention, the fiber output can be increased up to about 70 mW, corresponding to 270 pJ pulse energy, provided there is enough average power from the light source to be tested in a standard THz-TDS configuration.

Figure 7:
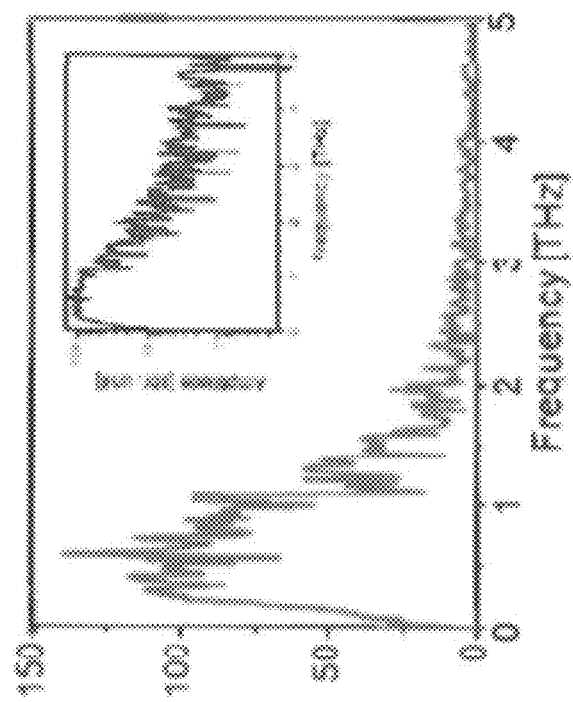
FIG. 7 depicts a measured THz pulse in air generated by a $LP_{02}$ fs-laser beam and the typical water absorption lines in accordance with one exemplary embodiment of the present invention.
Figure 7:
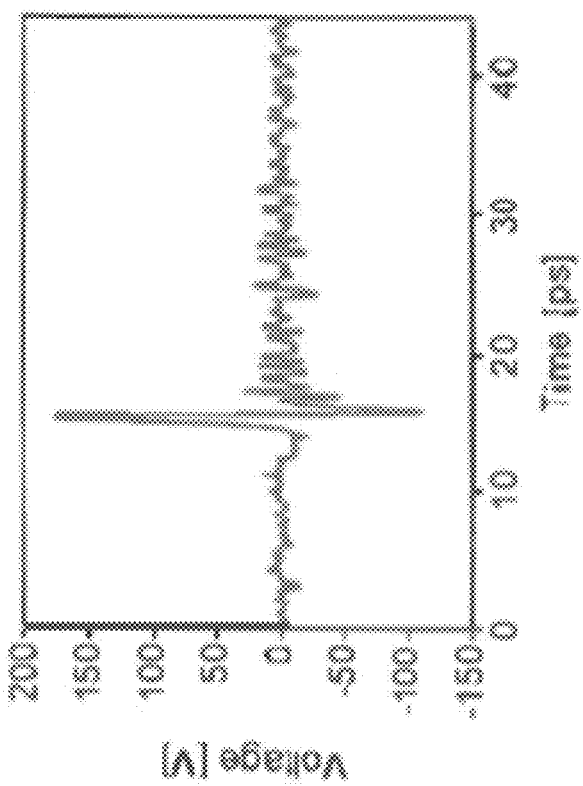

FIG. 7 (left) shows the very first measured THz pulse generated by the $LP_{02}$ fs-laser beam using a low-temperature grown GaAs photo-conductive switch as an emitter and also for detection. The THz pulse is propagating in ambient air. Although SNR of the FFT spectrum showing the typical water absorption lines (FIG. 7, right) is still low. This first result for a fiber delivery over 19 m nevertheless demonstrates the impact and capability of the novel technology with respect to fiber distance, simplicity, efficiency and compactness.

FIG. 7 depicts a measured THz pulse in air generated by a $LP_{02}$ fs-laser beam and the typical water absorption lines, in accordance with one exemplary embodiment of the present invention. As shown in FIG. 7 (left), the THz signal is measured at 70 mW (corresponding to 270 pJ pulse energy) of fiber output power. In FIG. 7 (right), the FFT-THz spectrum is shown, inset on a log-scale and shows spectral contents beyond 1 THz.

The exemplary embodiments of the present invention described herein provide a 19 m long fiber delivery for Ti:Sapphire fs-lasers having suitable potential in THz time domain spectroscopy. As described above, the effect of soliton propagation in a HOM fiber is exploited, in combination with a standard single-mode fiber, to deliver sub 100 fs pulses from a Ti:Sapphire laser fiber without pre-chirping the input pulse.

Utilizing the HOM fiber to investigate or facilitate solution propagation in the 0.8 µm wavelength range offers distinct advantages over known approaches with holey fibers. The much larger mode-field diameter of the HOM fiber over holey fibers facilitates its application to more intense light pulses, whereas the possible combination with conventional single-mode fibers enables very flexible dispersion management and high light coupling efficiencies. The potential of this technique for a wide range of fs-laser applications is demonstrated by applying the ultrashort pulse fiber delivery to a standard THz TDS system.

Embodiments of the present invention introduce THz radiation being generated and detected with infrared laser pulses delivered in the $LP_{02}$ mode. Embodiments disclosed herein show a simple and compact structure capable of self-management of dispersion and omission of the requirement for aligning sensitive optics for dispersion compensation. Embodiments of the present invention have the potential to be a powerful candidate for long distant fiber delivery for THz TDS applications in the 50 m to 100 m range. Other relevant embodiments may include 2-photon polymerization and mulitphoton endoscopic imaging.

Further embodiments of the present invention include the method of fiber delivery of sub-200 fs pulses to a mulitphoton fluorescence microscope system. Multiphoton fluorescence microscopy is a technique to use long wavelength light for multiphoton excitation of biological samples to obtain fluorescence from a highly localized volume of the sample. The fluorescence is collected by an optical arrangement and by raster scanning the sample an image can be generated. In many embodiments, a fiber delivery of fs pulses to a multiphoton fluorescence microscope will significantly improve the flexibility of integrating a fs lighsource with the microscope system. Furthermore, the use of a fiber delivery of fs pulses will enhance the efficiency of the optical system since the output of the fiber is diffraction limited.

In a more advanced system a fiber delivery may enable endoscopic multiphoton fluorescence microscopy where the delivery fiber is injected into a living biological sample i.e. in vivo. A fluorescence microscope image can be generated by raster scanning the tip of the fiber delivery over a deceased area of interest (in vivo) and by collecting the fluorescence using fiber.

While the foregoing is directed to embodiments of the present invention, other and further embodiments of the invention may be devised without departing from the basic scope thereof. It is also understood that various embodiments described herein may be utilized in combination with any other embodiment described, without departing from the scope contained herein. In addition, embodiments of the present invention may be further scalable, as particular applications may require.

What is claimed is:

1. An all-fiber delivery system for femtosecond laser pulses without pulse pre-chirping comprising:
   a first fiber with normal dispersion; and
   a higher order mode fiber with anomalous dispersion, the higher order mode fiber having a relative dispersion slope substantially equal to that of the first fiber and having an effective area of about 14.9 μm$^2$;

wherein the all-fiber delivery system is free of bulk optics and is suitable for producing a resulting higher order mode light as a free-space output;

wherein the higher order mode comprises one of $LP_{02}$, $LP_{03}$, or $LP_{04}$; and wherein the first fiber comprises one of a micro-structure fiber or a multi-mode fiber.

2. The all-fiber delivery system of claim 1, wherein the first fiber comprises a single mode fiber.

3. The all-fiber delivery system of claim 1, further comprising a mode converter between the first fiber and the higher order mode fiber.

4. The all-fiber delivery system of claim 3, wherein the mode converter comprises a long-period-grating mode converter.

5. The all-fiber delivery system of claim 1, wherein the laser pulses are generated by a mode-locked laser.

6. The all fiber delivery system of claim 1, further comprising a second mode converter at an output end of the higher order mode fiber in order to achieve a fundamental mode output beam.

7. The all fiber delivery system of claim 6, wherein the mode converter comprises a long-period-grating (LPG) mode converter.

8. The all-fiber delivery system of claim 6, wherein the mode converter comprises a phase plate written into the output end-face of the higher order mode fiber or mounted directly onto the output end-face of the higher order mode fiber.

9. The all-fiber delivery system of claim 1, wherein an output pulse from the all-fiber delivery system comprises pulses at less than about 200 femtoseconds.

10. The all-fiber delivery system of claim 9, wherein the energy of the output pulse is between about 1 pJ to about 10 nJ.

11. The all-fiber delivery system of claim 9, wherein an absolute value of the group delay dispersion of the first fiber is smaller than that of the higher order mode fiber when soliton formation occurs.

12. The all-fiber delivery system of claim 1, wherein a group delay dispersion of both the first fiber and the higher order mode fiber facilitate pulses under 200 fs at the output of the all-fiber delivery system when linear pulse propagation occurs.

13. An all-fiber delivery system without pre-chirping comprising: a mode-locked laser for generating laser pulses;
a single mode fiber with normal dispersion;
a long-period-grating mode converter; and
a higher order mode fiber with anomalous dispersion, the higher order mode fiber having a relative dispersion slope substantially equal to that of the first fiber and having an effective area of about 14.9 μm$^2$;
wherein the all-fiber delivery system is free of bulk optics, is suitable for producing a resulting higher order mode light as a free-space output, and propagates laser pulses in the 200-1300 nm wavelength range over 0.1-100 meters;
wherein the higher order mode comprises one of $LP_{02}$, $LP_{03}$, or $LP_{04}$; and
wherein the first fiber comprises one of a micro-structure fiber or a multi-mode fiber.

* * * * *